US008012495B2

(12) United States Patent
Luu et al.

(10) Patent No.: US 8,012,495 B2
(45) Date of Patent: *Sep. 6, 2011

(54) LOTION-TREATED TISSUE AND TOWEL

(75) Inventors: Phuong V. Luu, Appleton, WI (US);
David W. White, Clintonville, WI (US);
Jacob H. Propp, Oshkosh, WI (US);
Brian J. Schuh, Appleton, WI (US)

(73) Assignee: Georgia-Pacific Consumer Products LP, Atlanta, GA (US)

( * ) Notice: Subject to any disclaimer, the term of this patent is extended or adjusted under 35 U.S.C. 154(b) by 684 days.

This patent is subject to a terminal disclaimer.

(21) Appl. No.: 11/297,201

(22) Filed: Dec. 8, 2005

(65) Prior Publication Data
US 2006/0110432 A1    May 25, 2006

Related U.S. Application Data

(63) Continuation-in-part of application No. 10/141,442, filed on May 7, 2002, now Pat. No. 7,169,400.

(51) Int. Cl.
*A61K 9/00* (2006.01)
*A61K 8/02* (2006.01)
*A61K 9/70* (2006.01)

(52) U.S. Cl. ......... 424/400; 424/401; 424/423; 514/846

(58) Field of Classification Search .................. 424/400, 424/401, 443; 514/846
See application file for complete search history.

(56) References Cited

U.S. PATENT DOCUMENTS

| | | | |
|---|---|---|---|
| 4,029,598 A | 6/1977 | Neisius et al. | 436/163 |
| 4,078,071 A | 3/1978 | Walker | 514/399 |
| 4,231,370 A | 11/1980 | Mroz et al. | 604/361 |
| 4,705,513 A | 11/1987 | Sheldon et al. | 604/361 |
| 4,767,625 A | 8/1988 | Mitsuno et al. | 424/401 |
| 4,797,273 A * | 1/1989 | Linn et al. | 424/59 |
| 4,987,632 A | 1/1991 | Rowe et al. | 15/104.93 |
| 5,240,562 A | 8/1993 | Phan et al. | 162/158 |
| 5,427,696 A | 6/1995 | Phan et al. | 162/158 |
| 5,525,345 A | 6/1996 | Warner et al. | 424/402 |
| 5,607,760 A | 3/1997 | Roe | 442/375 |
| 5,624,676 A | 4/1997 | Mackey et al. | 424/414 |
| 5,665,426 A | 9/1997 | Krzysik et al. | 427/211 |
| 5,690,624 A | 11/1997 | Sasaki et al. | 604/361 |
| 5,705,164 A | 1/1998 | Mackey et al. | 424/400 |
| 5,720,966 A | 2/1998 | Ostendorf | 424/402 |
| 5,781,942 A | 7/1998 | Allen et al. | 4/623 |
| 5,830,487 A | 11/1998 | Klofta et al. | 424/402 |
| 5,869,075 A | 2/1999 | Krzysik | 424/414 |
| 5,871,763 A | 2/1999 | Luu et al. | 424/402 |
| 5,882,573 A | 3/1999 | Kwok et al. | 264/510 |
| 5,902,540 A | 5/1999 | Kwok | 264/555 |
| 5,904,298 A | 5/1999 | Kwok et al. | 239/135 |
| 5,945,910 A | 8/1999 | Gorra | 340/573.1 |
| 5,980,922 A | 11/1999 | Mackey et al. | 424/402 |
| 5,981,044 A | 11/1999 | Phan et al. | 428/212 |
| 5,994,414 A | 11/1999 | Franco et al. | 516/74 |
| 6,001,381 A | 12/1999 | Gordon et al. | 424/402 |
| 6,007,797 A | 12/1999 | Bell et al. | 424/59 |
| 6,183,763 B1 | 2/2001 | Beerse et al. | 424/404 |
| 6,207,014 B1 | 3/2001 | de Haut et al. | 162/164.7 |
| 6,210,695 B1 | 4/2001 | Beerse et al. | 424/404 |
| 6,238,682 B1 | 5/2001 | Klofta et al. | 424/402 |
| 6,258,368 B1 | 7/2001 | Beerse et al. | 424/404 |
| 6,270,783 B1 | 8/2001 | Slavtcheff et al. | 424/402 |
| 6,284,259 B1 | 9/2001 | Beerse et al. | 424/404 |
| 6,309,655 B1 | 10/2001 | Minnix | 424/401 |
| 6,352,700 B1 | 3/2002 | Luu et al. | 424/402 |
| 6,383,505 B1 | 5/2002 | Kaiser et al. | 424/407 |
| 6,482,423 B1 | 11/2002 | Beerse et al. | 424/404 |
| 6,488,943 B1 | 12/2002 | Beerse et al. | 424/401 |
| 6,733,766 B2 | 5/2004 | Gott et al. | 424/401 |
| 6,733,773 B1 | 5/2004 | Hsu et al. | 424/443 |
| 6,949,089 B2 | 9/2005 | Olson et al. | 604/385.01 |
| 2001/0006676 A1* | 7/2001 | Bret et al. | 424/443 |
| 2001/0028889 A1* | 10/2001 | Breton et al. | 424/401 |
| 2002/0002124 A1 | 1/2002 | Biedermann et al. | 510/218 |
| 2002/0031486 A1 | 3/2002 | Lunsmann et al. | 424/70.28 |
| 2002/0061500 A1 | 5/2002 | Collopy | 434/238 |
| 2003/0154904 A1 | 8/2003 | Klofta et al. | 116/206 |
| 2003/0206940 A1 | 11/2003 | Gott et al. | 424/443 |
| 2003/0211124 A1 | 11/2003 | Luu et al. | 424/401 |
| 2004/0039353 A1 | 2/2004 | Koenig et al. | 604/289 |
| 2004/0191118 A1 | 9/2004 | Mody | 422/56 |
| 2005/0008680 A1 | 1/2005 | Deckner et al. | 424/443 |
| 2005/0031847 A1 | 2/2005 | Martens et al. | 428/321.5 |
| 2009/0060966 A1 | 3/2009 | Tsuda | |

FOREIGN PATENT DOCUMENTS

| | | |
|---|---|---|
| EP | 0 875 233 A1 | 11/1998 |
| EP | 1 050 297 A2 | 11/2000 |
| JP | 5-156596 A | 6/1993 |
| WO | 95/06102 | 3/1995 |
| WO | 97/30216 | 8/1997 |
| WO | WO 97/30216 | 8/1997 |
| WO | 99/45771 A1 | 9/1999 |
| WO | 00/56346 A1 | 9/2000 |
| WO | 01/08640 A2 | 2/2001 |
| WO | 01/35906 A2 | 5/2001 |
| WO | 01/45613 A1 | 6/2001 |
| WO | 01/45615 A1 | 6/2001 |

OTHER PUBLICATIONS

Michael and Irene Ash, Handbook of Industrial Surfactants, 2000, 3rd Ed, vol. 2, pp. 1168 and 1397, Synapse Information Resources Inc., Endicott, NY.

* cited by examiner

*Primary Examiner* — Johann Richter
*Assistant Examiner* — Abigail Fisher
(74) *Attorney, Agent, or Firm* — Laura L. Bozek

(57) ABSTRACT

A paper towel includes: (a) a cellulosic towel web; and (b) a lotion emulsion disposed on the towel web. The lotion emulsion is substantially liquid at room temperature and includes a polar emollient and a non-polar emollient as well as a surfactant composition comprising a nonionic surfactant; wherein the emollients and surfactant composition are selected such that the lotion emulsion is immobilized on the towel web in a semi-solid or solid state and the lotion emulsion is capable of forming an aqueous gel upon contact with water. Preferably, the lotion emulsion is a waterless microemulsion which is also capable of forming an aqueous microemulsion with water.

32 Claims, 2 Drawing Sheets

LOTION-TREATED TISSUE AND TOWEL

CLAIM OF PRIORITY

This application was a continuation-in-part of application U.S. Ser. No. 10/141,442 entitled "Waterless Lotion and Lotion-Treated Substrate," filed on May 7, 2002, now U.S. Pat. No. 7,169,400. The disclosure of U.S. patent application Ser. No. 10/141,442 is hereby incorporated in its entirety into this application by reference thereto and priority thereof is claimed in accordance with 37 CFR 1.78.

TECHNICAL FIELD

The present invention relates to a paper tissue and towel having a skin-conditioning lotion thereon that is predominantly comprised of an emollient composition and a surfactant composition. In a preferred embodiment, the lotion is a waterless micro-emulsion lotion which is substantially liquid at room temperature and semi-solid or solid upon contact with the towel such that the lotion becomes immobilized on the towel surface. The immobilized lotion emulsion is capable of forming an aqueous gel upon contact with water when the towel is used. Most preferably, the lotion is also capable of forming an aqueous emulsion when mixed with water.

BACKGROUND

Adequate skin care is a simple and effective means for maintaining not only healthy skin but overall health as well. Damaged skin fails to protect against toxic, irritating substances and germs in the environment. Cleaning, moisturizing, and nourishing skin is accordingly extremely important; indeed, the literature is replete with cleansing and moisturizing lotions for restoring and maintaining the skin's healthy state. Skin care is particularly important for food service employees and health care workers who must wash their hands frequently.

Cellulosic substrates coated with lotions are well known in the art. For example, U.S. Pat. No. 5,665,426 to Krzysik et al., is directed towards a lotion formula that can be applied to a tissue, which transfers the lotion to the user's skin in order to reduce irritation and redness. The lotion composition of '426 is solid at room temperature and is applied to substrates by rotogravure printing process. U.S. Pat. No. 5,871,763 to Luu et al., as well is directed towards a lotion formula that has to be melted prior to its application to a substrate for skin care treatment. The lotion composition of '763 is melted by the heat produced by the hands of a user of the cellulosic substrate to enable the lotion's transfer to the user's skin. Another lotion treated substrate is described in U.S. application Ser. No.10/483,633 (Publication No. US 2005/0031847), where two separate and distinct phases, lipid and aqueous, are applied to a substrate to facilitate cleansing of skin. Further, there is described in U.S. Pat. No. 4,987,632 to Rowe et al., a cleaning wipe treated with a composition containing detergent, which is leached out upon contact with water. See also U.S. Pat. No. 5,525,345 to Warner et al.

There are also known lotions containing anti-microbial and pH balancing agents to protect and condition skin. For example, U.S. Pat. No. 6,238,682 to Klofta et al. is directed towards a tissue treated with anhydrous skin lotion, which is semi-solid at room temperature, containing antimicrobial components in addition to hydrophilic solvents and surfactants. See also U.S. Pat. No. 6,352,700 to Luu et al., which is directed towards a substrate treated with a lotion, which is solid at room temperature and contains a skin pH balancing compound for maintaining a proper skin acid mantle. Other lotions containing antimicrobial agents include U.S. patent application Ser. No. 10/608,661 (Publication No. US 2004/0039353), which is directed towards wet wipes containing a Yucca species extract as an antimicrobial agent; U.S. patent application Ser. No. 09/851,273 (Publication No. US 2002/0031486), which is directed towards an antimicrobial cleansing composition, containing little or no volatile alcohol, that may be used alone or in combination with lotions and a like; U.S. patent Application Ser. No. 09/738,365 (Publication No. US 2002/0002124), which is directed towards an antimicrobial cleansing compositions that has a pH of from about 2 to about 5.5.; U.S. Pat. No. 6,383,505 to Kaiser et al which is directed towards an antimicrobial lotion for topical use in a form of oil-in-water emulsion; additionally, similar subject matter is disclosed in U.S. Pat. No. 6,482,423 to Beerse et al.; U.S. Pat. No. 6,488,943 to Beerse et al.; U.S. Pat. No. 6,284,259 to Beerse et al.; U.S. Pat. No. 6,258,368 to Beerse et al.; U.S. Pat. No. 6,183,763 to Beerse et al.; and U.S. Pat. No. 6,210,695 to Beerse et al. as well.

Lotions that are solid or semi-solid at room temperature and require melting prior to application to substrates, also referred to as "hot" lotions, have numerous drawbacks. For one, semi-solid or solid lotions require cumbersome and costly heating systems such as melting tanks and heated equipment to deliver the lotion to the substrate. Additionally, cleaning of build-up and solidification of lotion on the conveyer roll of the production line during and after the application process is another cumbersome and costly procedure incurred in connection with so called "hot" lotions. Incorporation of water-based additives in such lotions is difficult, due to phase separation and lack of uniform distribution of the additive in the lotion, either before or after application onto the product substrate. Further, "hot" lotions have a tendency to become stiff when excess lotion is used, and the final products tend to leave smears when used.

It has been found in accordance with the present invention that an emulsion lotion can be applied to paper towel at room temperature and immobilized on the towel surface. The emulsion composition is selected such that it forms an aqueous gel lotion when mixed with water, which gel is readily transferred to a user's skin when the product is used.

SUMMARY OF THE INVENTION

The present invention provides lotioned tissue and towel with enhanced skin care and anti-microbial activity. Numerous attributes make the lotioned products of the invention especially suitable for towels used by health care and food service workers. Waterless micro-emulsion is immobilized on the substrate, but is readily restorable to transferable form when wetted. Thus, when contacted with wet hands, for example, the lotion is readily transferred to the hands of a user. The lotion also forms a glutinous gel when mixed with water; a highly desirable characteristic for lotion.

Preferred lotions do not substantially impair basesheet absorption capacity, but increase WAR times. This latter feature promotes lotion transfer to the skin as well, since a user will rub the towel longer when drying his or her hands. When anti-microbial activity is desired, effective transfer is extremely important as will be appreciated by one of skill in the art.

There is thus provided in one aspect of the invention a lotion-treated substrate suitable for tissue or towel including: (a) a cellulosic web; and (b) a lotion emulsion disposed on the web, the lotion emulsion including a polar emollient and a non-polar emollient as well as a surfactant composition comprising a nonionic surfactant; (c) wherein the lotion emulsion is substantially liquid at room temperature; (d) the emollients and surfactant composition are selected such that the lotion emulsion is immobilized on the towel web in a semi-solid or solid state; and (e) wherein further the lotion emulsion is capable of forming an aqueous gel upon contact with water. Typically, the emollient composition comprises a polar emollient such as a polar polyhydroxy emollient selected from propylene glycol, glycol, glycerol, sorbitol, diethylene glycol, methylene glycol, polypropylene glycol and polyethylene glycol, as well as a compatible non-polar emollient. The non-polar emollient may be selected from an aromatic or linear ester, Guerbet ester, mineral oil, squalane, squalene and liquid paraffin. The surfactant composition typically comprises a non-ionic surfactant which may be selected from PEG-20 methyl glucose sesquistearate, PPG-20 methyl glucose ether, PPG-20 methyl glucose ether distearate, PEG-20 methyl glucose distearate, PEG-120 methyl glucose dioleate and ethoxylated methyl glucose having from about 10 to about 20 repeating ethoxy units, as well as a co-surfactant. The co-surfactant may be a fatty alcohol selected from $C_{12}$-$C_8$ fatty alcohols, behenyl alcohol, iso cetyl alcohol and iso stearyl alcohol. The lotion emulsion consists predominantly, 50% by weight or more, of emollient and surfactant in a preferred embodiment.

In one preferred embodiment, the lotion emulsion is a waterless micro-emulsion and the web is treated with the lotion emulsion in an amount of from about 0.1% to about 25% by weight of the dried fiber. In most cases, the web is treated with the lotion emulsion in an amount of from about 0.5% to about 20% by weight of the dried fiber.

The lotion emulsion may further comprise an anti-microbial agent such as 2,4,4'-trichloro-2'-hydroxydiphenyl ether (triclosan), 3,4,4'-trichlorocarbanilide (triclocarban), 3,4,4'-trifluoromethyl-4,4'-d-ichlorocarbanilide (cloflucarban), 5-chloro-2-methyl-4-isothiazolin-3-one, iodopropynlbutylcarbamate, 8-hydroxyquinoline; 8-hydroxyquinoline citrate, 8-hydroxyquinoline sulfate, 4-chloro-3,5-xylenol(chloroxylenol), 2-bromo-2-nitropropane-1,3-diol, butoconazole, nystatin, terconazole, nitrofurantoin, phenazopyridine, acyclovir, clortrimazole, chloroxylenol, chlorhexidine, chlorhexidine gluconate, miconazole, terconazole, butylparaben, ethylparaben, methylparaben, methylchloroiso-thiazoline, methylisothiazoline, mixtures thereof, and the like. The micro-emulsion lotion optionally includes an additive selected from the group of fragrances, preservatives, medicinal agents, humectants, natural therapeutic oils, botanical extracts, natural or synthetic powders, and soothing agents and the web may include a wet strength agent.

In another aspect of the invention, there is provided a lotion-treated substrate suitable for tissue or towel comprising: (a) a cellulosic web; and (b) a waterless micro-emulsion which is substantially liquid at room temperature immobilized on the web in a semi-solid or solid state; (c) wherein the waterless micro-emulsion consists essentially of a polar emollient, a non-polar emollient and a surfactant composition comprising a nonionic surfactant; and (d) wherein further the waterless micro-emulsion is capable of forming an aqueous micro-emulsion upon contact with water.

In yet another aspect of the invention, there is produced a lotion-treated substrate suitable for tissue or towel comprising: (a) a cellulosic web; and (b) a waterless micro-emulsion which is substantially liquid at room temperature immobilized on the web in a semi-solid or a solid state; wherein the micro-emulsion comprises a polar emollient, a non-polar emollient, a co-surfactant and a non-ionic surfactant.

In still yet another aspect of the invention, there is provided a method of making a lotion-treated substrate suitable for tissue or towel comprising: (a) preparing a lotion emulsion including a polar emollient, a non-polar emollient and a surfactant composition comprising a non-ionic surfactant; (b) treating a cellulose web with the lotion emulsion; wherein the emollient composition and surfactant composition are selected such that the lotion emulsion is immobilized on the towel web in a semi-solid or solid state and wherein the lotion emulsion is capable of forming an aqueous gel upon contact with water. Typically, the micro-emulsion is applied to the web by way of spraying or printing at room temperature.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification.

DETAILED DESCRIPTION

Figure 1:
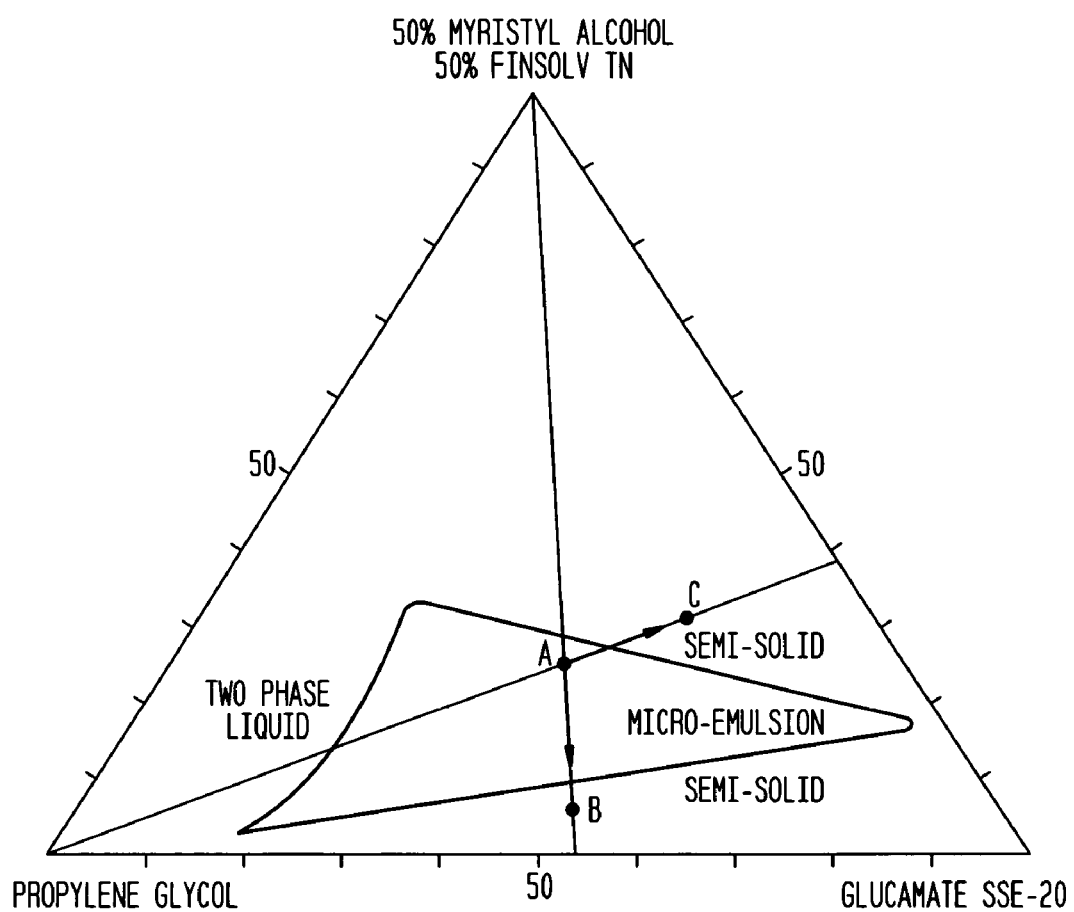
FIG. 1 is a partial phase diagram of the composition of Example I showing the phase characteristics of a waterless micro-emulsion.

The invention is described in detail below for purposes of illustration only. Modifications within the spirit and scope of the invention, set forth in the appended claims, will be readily apparent to one of skill in the art. As used herein, terminology and abbreviations have their ordinary meaning; for example, "cps" refers to centipoises.

"Aqueous gel" refers to viscous lotion/water compositions typically having a room temperature viscosity of above about 500 cps at room temperature and typically above about 1000 cps at room temperature. Preferred lotion compositions form gels of more than 1500 cps at room temperature as is seen in Table 2 below.

The invention relates, in part, to a substrate treated with a waterless micro-emulsion lotion, which is substantially liquid at room temperature. For the purposes of the present invention, room temperature is a temperature of from about 20° C. to about 25° C. The lotion formula of the present invention undergoes an in-situ phase change from liquid to semi-solid, finely divided, uniformly dispersed form upon contact with the substrate, for example, the fibers of the web. This property is important in preventing liquid lotion migration into the substrate or the packaging, and in enhancing the lubricious, soft, and non-greasy feeling of the lotioned substrate. Lotion in the substrate is readily transferred to the user's skin by the friction from wiping, body heat and the addition of water to provide the benefits to the skin surface.

Furthermore, this lotion formula is also termed "cold" lotion since it is a liquid at room temperature. The term "hot" or "cold" lotion refers to either the lotion form being solid ("hot") or liquid ("cold") at room temperature and lotion application temperature either higher ("hot") or at room temperature ("cold"). Application of a cold lotion does not require cumbersome and expensive heated delivery equipment. Rather, the lotion can be applied easily by any available technology such as spraying, printing, coating, extrusion or other techniques. The micro-emulsion or "cold" lotion contains an external continuous non-polar or polar emollient, an internal discontinuous polar or non-polar emollient, a surfactant and a mixture of fatty alcohol co-surfactants. The lotion may also contain optional ingredients, including plant extracts, perfume and a medicinal agent.

The lotion of the present invention alleviates handling/application issues associated with a "hot" lotion and improves the product softness and absorbency of the lotion treated substrate. This is achieved by the present waterless, hydrophilic "cold" lotion, which is liquid at room temperature, that can be applied to the substrate without heating equipment. The lotion is capable of an in-situ phase change from liquid to a semi-solid form upon contact with the web fibers which when loaded prevents lotion free flow and migration. In addition to these advantages over a "hot" lotion, the lotioned product of the present invention also provides a lubricious, soothing non-greasy feeling, gentle and effective cleansing, skin healing and moisturizing benefit for the user's skin. Further, the lotion composition is able to incorporate typical cosmetic additives, preservatives and anti-bacterial agents regardless of the water solubility of the additive. Finally, facial tissue products made from "hot" lotion are usually not recommended for cleaning transparent materials, such as eyeglasses, due to the "hot" lotion leaving a translucent or opaque smear. The present "cold" lotion treated substrates do not suffer this deficiency.

The present invention relates, in part, to a substrate treated with a waterless, micro-emulsion lotion, which is liquid at room temperature. The composition preferably includes four basic components: a polar emollient, non-polar emollient, co-surfactant, and non-ionic surfactant.

Preferred polar emollients include a polyhydroxy emollient. Preferred polyhydroxy emollients include propylene glycol, glycol, glycerol, sorbitol, diethylene glycol, methylene glycol, polypropylene glycol, polyethylene glycol, and the like.

Preferred non-polar emollients include an aromatic or linear ester, Guerbet ester, mineral oil, squalane, squalene, liquid paraffin and the like.

The polar or non-polar emollient is either in the continuous outer phase or in the discontinuous internal phase of the micro-emulsion.

Preferred co-surfactants include fatty alcohols. Preferred fatty alcohols include $C_{12}$ to $C_{18}$ fatty alcohols, behenyl alcohol, iso cetyl alcohol, and iso stearyl alcohol.

Preferred non-ionic surfactants include PEG-20 methyl glucose sesquistearate, PPG-20 methyl glucose ether, PPG-20 methyl glucose ether distearate, PEG-20 methyl glucose distearate, PEG-120 methyl glucose dioleate, ethoxylated methyl glucose having from about 10 to about 20 repeating ethoxy units, and the like.

The compositions of the present invention are preferably chosen to lie within the micro-emulsion region of a given formulation. All percentages, ratios, and proportions of the ingredients within the compositions of the present invention are determined by the micro-emulsion region of a ternary phase diagram of the polar emollient/non-polar emollient/co-surfactant/non-ionic surfactant formulations (PE/NPE/COS/NIS). Outside of the micro-emulsion region on the low percent side of the polar or non-polar emollients, a semi-solid or solid region is preferably present (see FIG. 1). A micro-emulsion is thermodynamically stable and is essentially transparent in the visible region of the spectrum, which typically indicates that particle size diameter is preferably less than about 0.1 micron, or so. When the particle size diameter is greater than about 3,200 A (about 0.32 micron), the liquid is no longer considered a micro-emulsion but is an emulsion which can often appear turbid and be thermodynamically unstable. The micelle structure of a micro-emulsion is either a "direct" type (head out/tail in) or an "inverse" type (head in/tail out). The liquid micro-emulsion increases the surface area of the lipophilic constituent so it contributes significantly to the utility of the present composition in neat form. Fluidity on the skin surface, small particle size, high surface area and high hydrophilic character, are highly desirable properties for cleansing purposes either when the substrate is used by itself or when lotioned products are rewet with water. Any combination or proportion of these ingredients which produces a micro-emulsion can be used.

An important aspect of this invention is when the liquid lotion contacts the fibers or non-woven substrate, it undergoes an in-situ phase change from liquid to semi-solid or solid form. This change results when the substrate web surface fibers absorb the continuous outer phase of the micro-emulsion, while the continuous outer phase of the micro-emulsion may be a non-polar or polar emollient. Consequently, the percent of the outer phase of the micro-emulsion within the composition is reduced, resulting in increase in the percent of the internal phase of the micro-emulsion. This change in the micro-emulsion composition can be observed in FIG. 1. The original micro-emulsion is substantially liquid at room temperature and is indicated by point A, which is located inside the micro-emulsion region in FIG. 1. Once the percent of the micro-emulsion internal layer increases and the micro-emulsion overall composition changes, the phase of the micro-emulsion changes. The new state of the micro-emulsion is indicated by points B and C located in the semi-solid region of FIG. 1. This unique and special characteristic of phase change represents an advantage of the invention, in contrast to the lotion of the prior art, in both application process and product performance.

In the application process, the lotion of the invention uses simple and low cost technology relative to the prior art because it is waterless and substantially liquid at room temperature. In contrast, most of the lotions used for treated tissue or non-woven substrate in the prior art are in semi-solid or solid form at room temperature, which requires heated equipment to deliver lotion to the substrate. Furthermore, any delivery technology available can be easily used for application of the lotion of the present invention without heating equipment, such as an air atomized spray coating, brush coater, curtain coater, and direct or offset gravure coating. Cleaning the production line during or after lotion application process due to build-up and solidification of lotion on the conveyer roll is also a serious issue with "hot" lotions. This issue is minimized with the present invention lotion; and in addition, at the converting line, the liquid lotion may act as a lubricant and impede adhesion of "stickies" (gummy deposits from recycle fiber basesheet) on the embossing rolls to improve the converting process and production rate.

The micro-emulsion is liquid at room temperature, but when in contact with the paper or non-woven substrate, the lotion phase changes to semi-solid form. This unique property provides for the liquid "cold" lotion advantages which are primarily associated with "hot" lotion such as: (1) retaining more lotion on the substrate surface; (2) impeding penetration of the lotion into the web without requiring an immobilizing agent; (3) reducing the amount of lotion applied required to enhance the product performances; and (4) reducing the impact of lotion on the physical properties of the tissue. Additionally, if necessary, a higher level add-on of the present lotion can be applied to the substrate as compared to the "hot" lotion due to the liquid form of the "cold" lotion at room temperature. In this case, the hydrophilic nature of the "cold" lotion product will remain resulting in better cleansing or enhanced skin care benefits, in contrast to the hydrophobic "hot" lotion. These cold lotions do not suffer from the common deficiencies of hot lotions wherein it is observed that use of too much "hot" lotion can result in the product becoming stiff.

The ability of the continuous outer phase to include either polar or non-polar components provides advantages to the present invention. Both polar and non-polar emollients contribute to the ability of the present invention to accommodate a wide range of compatibility with various additives such as preservatives, anti-bacterial agents, natural therapeutic oils, soothing agents, whether they are soluble or not in the polar or non-polar emollient. In other words, the formulations of the present invention may be designed to be effective at promoting numerous consumer benefits. For example, in a wiper product containing a high add-on level (100% to 300%) of the present lotion for cleansing oil-based dirt or grease on the skin, the preferred lotion composition includes a polar emollient outer phase/non polar oil internal phase/hydrophilic surfactant with co-surfactant fatty alcohol $C_{14}$ to $C_{18}$. After application of the micro-emulsion to the cellulosic substrate, the weight percent of the outer phase polar emollient is preferably very low relative to the non-polar internal phase emollient as the polar phase is strongly absorbed by the cellulosic fibers. In wiping oily skin surfaces, the product releases the non-polar emollient (as a carrier) and the nonionic surfactant. This combination emulsifies the oil-based dirt or grease on the skin and, by encapsulating it inside the micelle structure after wiping, carries it into the internal phase of the cleaning formulation without leaving a non-polar oil phase on the skin. This formulation is well-suited for cleaning of oils. We prefer that the outer phase be polar because the grease or oil goes into the non-polar phase on the wipe and thus may be removed. This micro-emulsion with a polar outer phase is believed better for cleansing oil from the skin surface than using a lotion formulation of non-polar oil emollient outer phase/polar emollient internal phase/nonionic surfactant plus co-surfactant because lotions having a non-polar continuous phase micelle structure contacts the skin with the oily phase, thus the non-polar outer phase only dissolves the contaminant and, thus, can leave both the oil-based contaminant and non-polar oil phase on the skin surface. Thus a product treated with formulations having continuous non-polar phases are less desirable for removal of oils or greasy material because non-polar liquid is often left on the skin after wiping.

Conventional liquid lotions for a tissue substrate (oil-in-water emulsion) are well known in the art, but generally have at least 70-80% water in the formula. Water in the lotion formula is undesirable for post treatment of the tissue product because: (1) it limits the amount of lotion that can be applied to the substrate due to the lotion having a low percent solid; (2) the large negative impact on the product's physical properties and problems encountered at the treatment line due to water rewetting and weakening of the paper; and (3) the need to install an oven, or other drying device, on the treatment line for removal of the water in the substrate. The present invention formula is waterless but still maintains the ability of incorporating water-soluble additives into the polar phase, plus easily adding oil soluble additives into the non-polar phase of the lotion. This capability is also an advantage of the "cold" lotion compared to "hot" lotion. Incorporating water-based additives in "hot" lotion is very difficult, due to phase separation and loss of uniform distribution of the additive in the lotion, either before or after application onto the product substrate. Water content in "hot" lotion of up to 10 or 15 percent might eliminate the phase separation problem, but controlling and maintaining water content in a lotion formulation at high temperature (about 75° C. to about 90° C.) during process application can be a difficult task. This disadvantage is avoided by the "cold" lotion of the present invention.

The invention relates to a tissue, towel or napkin, optionally wet-strengthened, or wipe or nonwoven material, such as that used for diaper, incontinence and menstrual pad coverstock that is treated with a nongreasy-feeling lotion. The lotion has the effect of making the treated substrate feel nongreasy, reducing chaffing and irritation when the substrate is applied to the skin, and imparting a lubricious feel. Skin care benefits of the lotionized substrate are expressed whether the invention is used dry or prewetted with water.

The lotion can optionally include a therapeutic amount of a medicinal agent. Medicinal agents include medicines, antipathogenic agents, antimicrobial agents, antibacterial agents, antiviral agents, disinfectants, analgesics, other types of medicine having suitable medicinal properties, and the like. For example, an antibacterial agent can be present in an amount of from about 0.01% to about 10%, preferably from about 0.05% to about 5%, of the lotion. Suitable antimicrobial agents include those effective against human pathogens, such as *escherichia coli, staphylococcus aureus, salmonella chloreraesuis, salmonella typhi, pseudomonas aeruginosa, pseudomonas cepacia*, and the *candida* species, including *albicans*. Specific antimicrobial agents suitable for use in the lotion of the invention include 2,4,4'-trichloro-2'-hydroxy-diphenyl ether (triclosan); 3,4,4'-trichlorocarbani lide (triclocarban); 3,4,4'-trifluoromethyl-4,4'-d-ichlorocarbanilide (cloflucarban); 5-chloro-2-methyl-4-isothiazolin-3-one; iodopropynlbutylcarbamate; 8-hydroxyquinoline; 8-hydroxyquinoline citrate; 8-hydroxyquinoline sulfate; 4-chloro-3,5-xylenol(chloroxylenol); 2-bromo-2-nitropropane-1,3-diol; diazolidinyl urea; butoconazole; nystatin; terconazole; nitrofurantoin; phenazopyridine; acyclovir; clortrimazole; chloroxylenol; chlorhexidine; chlorhexidine gluconate; miconazole; terconazole; butylparaben; ethylparaben; methylparaben; methylchloroisothiazoline; methylisothiazoline; a mixture of 1,3-bis(hydroxymethyl)-5,5-dimethylhydantoin and 3-iodo-2-propynyl butyl carbamate; oxyquinoline; EDTA; tetrasodium EDTA; p-hydroxyl benzoic acid ester; alkyl pyridinum compounds; quaternary ammonium compounds, such as coco phosphatidyl PG-dimonium chloride; mixtures thereof; and the like. Other preferred antimicrobial agents include derivatives of substituted N-alkyl imidazolines disclosed in U.S. Pat. No. 4,078,071 to Walker, issued Mar. 7, 1978, which is incorporated hereby in reference in its entirety.

An anti-viral agent can be present in an amount of from about 0.025% to about 5%, preferably from about 0.05% to about 2.5%, of the lotion. Suitable anti-viral agents include those effective against, or at least retardant toward Corona virus, Picorna virus, Rhino virus, Herpes simplex, Herpes genitalis, Herpes labialis, Respiratory Syncytial Virus (RSV), Para influenza, Cytomegalovirus, Adenovirus, Condyloma and certain synergistic disease states that can involve a virus and a protozoa or a virus and any unfriendly enzymes, e.g., protease, lipase and amylase, that cause a compromised skin as a precursor state for a viral infection to occur. Specific anti-viral agents suitable for use in the lotion of the present invention include bioflavonoids such as hesperitin, naringin, catechin and certain selected amino acids of leguminous origin such as L-canavanine and an analog of L-arginine; dicarboxylic acids such as malonic, glutaric, citric, succinic, and diglycolic acids; alpha hydroxy carboxylic acid such as D-galacturonic acid from Sterculia urens; neem seed oil (Azadirachta indica) in its un-denatured form; sandalwood oil (Santalum album L.) in its un-denatured form. Optionally, the anti-viral agent could be admixed with at most about 50% by weight of the anti-viral agent of a protease inhibitor such as zinc oxide or other suitable zinc salt.

The lotion can optionally include fragrance. The fragrance can be present in an amount of from 0.01% to about 2%. Suitable fragrance includes volatile aromatic esters, non-aromatic esters, aromatic aldehydes, non-aromatic aldehydes, aromatic alcohols, non-aromatic alcohols, heterocyclic aroma chemicals, and natural floral fragrances, such as blossom, carnation, gardenia, geranium, iris, hawthorne, hyacinth and jasmine.

The lotion can optionally include natural or synthetic powder like talc, mica, boron nitride, silicone, or mixtures thereof.

The substrate web of the present invention optionally includes a wet strength agent. The wet strength agent includes temporary as well as permanent wet strength agents. Suitable wet strength agents include glyoxal; glutaraldehyde; uncharged chemical moieties selected from a group consisting of dialdehydes, aldehyde-containing polyols, uncharged aldehyde-containing polymers, and cyclic ureas and mixtures thereof, and aldehyde-containing cationic starch; mixtures of polyvinyl alcohol and salts of multivalent anions, such as boric acid or zirconium ammonium carbonates; glyoxalated polyacrylamide; polyamide-epichlorohydrin; polyamine-epichlorohydrin; urea-formaldehyde; melamine-formaldehyde; polyethyleneimine; and latex emulsions.

The lotion composition can include other optional components typically present in lotions of this type. These optional components include a botanical extract, such as aloe extract, avocado oil, basil extract, sesame oil, olive oil, jojoba oil, chamomile extract, eucalyptus extract, peppermint extract, as well as animal oils such as emu oil, cod liver oil, orange roughy oil, mink oil, and the like. The lotion of the present invention can also optionally include a humectant. Humectants are hygroscopic materials with a two-fold moisturizing action including water retention and water absorption. Humectants prevent the loss of moisture from skin and help to attract moisture from the environment. Preferred humectants include glycerol, hydrolyzed silk, ammonium lactate, hydroxypropyltrimonium hydrolyzed silk, hydroxypropyl chitosan, hydroxypropyltrimonium hydrolyzed wheat protein, lactamidopropyltrimonium chloride, and ethyl ester of hydrolyzed silk. The botanical extract, animal oil or humectant is preferably present in an amount of less than about 3% when used in the base formulation of the lotion. Further optional components include a skin refreshing agent such as encapsulated water in oil, eucalyptus oil, and menthol oil. All of these optional materials are well known in the art as additives for such formulations and can be employed in appropriate amounts in the lotion compositions of the present invention by those skilled in the art.

The towel web of the present invention can be any suitable cellulosic substrate web, optionally wet-strengthened, and optionally including synthetic fibrous material such as meltblown polyethylene, polypropylene, copolymers of polyethylene and, in addition to cellulosic fiber. The substrate also may be embossed.

The present invention includes a web of cellulosic fibers treated on at least one side thereof, preferably in an amount of from about 0.1% to about 25%, more preferably from about 0.5% to about 20%, by weight of the dried fiber web with the lotion of the present invention.

The cellulosic substrate can be prepared according to conventional processes (including TAD, CWP and variants thereof) known to those skilled in the art. The substrate may be creped or uncreped. Lotion can be applied to the substrate according to conventional application methods known to those skilled in the art.

EXAMPLES

Formulations of the waterless lotion of the present invention were prepared in which, the components, their ratios and the conditions selected to provide micro-emulsion subject to in-situ phase change upon contact with a cellulosic substrate were varied as shown in the following Examples.

In preparing each formulation the following, a general procedure was used. The polar phase propylene glycol was mixed with surfactant and co-surfactant in a heated container at about 60° C. to about 70° C. until the chemicals were completely melted. The non-polar oil phase was added to the mixture with moderate agitation for about 10 minutes, then cooled to room temperature. At this point the lotion was in clear liquid form and ready to apply to the substrate. The micro-emulsion formed spontaneously without the need for a high shear mechanical device and is stable indefinitely.

Examples 1-7

Examples 1 to 7 were prepared in accordance with the present invention.

These lotion formulas were liquid at room temperature, transparent, very stable and accordingly the lotion ingredient ratios were inside the micro-emulsion region of phase diagrams such as FIG. 1 which is a partial phase diagram of the composition of Example 1. Surprisingly, the lotion of the present invention is characterized as having a good hand-feel perception and non-greasy hand-feel, which is thought to be due to the particle size of the micro-emulsion being too small to be detected in the oil phase by the fingertips.

TABLE 1

| Ingredients | Ex. 1 (%) | Ex. 2 (%) | Ex. 3 (%) | Ex. 4 (%) | Ex. 5 (%) | Ex. 6 (%) | Ex. 7 (%) |
|---|---|---|---|---|---|---|---|
| Propylene glycol | 35 | 35 | 5 | 15 | 15 | 30 | 35 |
| Finsolv TN[1] | 12.5 | 0 | 16 | 0 | 30 | 15 | 0 |
| Carnation oil[2] | 0 | 0 | 0 | 0 | 0 | 0 | 12.5 |
| Isopropyl myristate | 0 | 15 | 0 | 30 | 0 | 0 | 0 |
| Lambert CE 2000[3] | 0 | 0 | 4 | 0 | 0 | 0 | 0 |
| Myristyl alcohol($C_{14}$) | 12.5 | 15 | 0 | 0 | 0 | 0 | 12.5 |
| Kalcol 1618[4] | 0 | 0 | 7.5 | 0 | 5.5 | 5.5 | 0 |
| Glucam P-20 Distearate[5] | 0 | 0 | 67.5 | 0 | 49.5 | 49.5 | 0 |
| Glucamate SSE-20[6] | 40 | 35 | 0 | 55 | 0 | 0 | 40 |

[1]Finsolv TN: $C_{12}$-$C_{15}$ alkyl benzoate ester from Finetex Inc.
[2]Carnation: Mineral oil from Witco Corp.
[3]Lambert CT 2000 - tri-octyldodecyl-citrate (Guerbet ester) from Lambert Technologies.
[4]Kalcol 1618: Mixture 50/50 of cetyl alcohol (C16) and stearyl alcohol (C18) from Kao Corp.
[5]Glucan P-20 Distearate: PEG-20 methyl glucose distearate from Amer-chol.
[6]Glucamate SSE-20: PEG-20 methyl glucose sesquistearate from Amer-chol.

Example 8

The lotion prepared in Example 1 was applied to a tissue basesheet at a 5% add-on level, then converted to a two ply tissue product. The product was tested for the amount of lotion transferred to the skin. The results were compared with commercially available lotioned tissues by comparing the light reflection of cold lotion residual on glass relative to that from two other products. The scattering of light caused by lotion smeared onto the glass microscope slide was measured by using the UV/visible spectrophotometer in the wavelength region from 700 nm to 400 nm. Lotion was transferred to the slide by holding it between two layers of lotioned tissue for 30 seconds and then rubbing the tissue over the slide 20 times in 15 seconds. The lotion smeared glass slide was placed in the sample beam of a double beam UVNisible spectrometer to measure the light scattering. The results show that scattering of light caused by lotion smeared onto the slide rubbed with the tissue treated with the lotion in Example 1, looked identical to the control (untreated tissue). However, the two commercially available lotioned facial tissue products tested produced a significant amount of light scattering compared to the lotioned tissue of the present invention. In fact, the containers for these commercial products specifically state "not recommended for cleaning eyeglasses." In addition, from the lab test result, the amount of lotion transferred by the lotioned substrate of the present invention to the skin was measured to be about 4.2 mg/cm$^2$.

The lotioned substrate product of the present invention was able to transfer lotion to the skin for enhancing skin care benefits, while also being able to "wipe eyeglasses and still maintain clear vision." These properties of the present invention represent significant advantages over the lotioned facial tissues of the prior art.

The waterless emulsion compositions of the present invention have numerous attributes which make them particularly suitable for paper towels. For one, the waterless micro-emulsions form low viscosity aqueous micro-emulsions with relatively small amounts of water such that an immobilized lotion on the substrate is restorable to readily transferable form when wetted or mixed with water. Thus, when contacted with wet hands of a paper towel user, for example, the lotion is readily transferred from the towel to the skin of a user.

Another unique characteristic of the invention is that the lotion emulsions are capable of forming glutinous gels with water as the amount of water mixed with the lotion is increased. Glutinous gels are generally more viscous and full-bodied than liquids, thus being more desirable as hand lotions.

Details as to these characteristics appear in Examples 9-16 below.

Examples 9-16

The composition of Example 1 was mixed with water and tested for viscosity using a Brookfield Digital Viscometer at 73° F. Examples 9, 10,11 and 16 were tested with a No. 2 spindle, while Examples 12, 13, 14 and 15 were tested with a No. 5 spindle. Details as to composition and test conditions appear in Table 2 below.

TABLE 2

Aqueous Phasing Properties

| Example #/ Description | Spindle # | Speed (RPM) | Viscosity (cps) | Appearance and Properties |
|---|---|---|---|---|
| 9/100% Lotion Example #1 | 2 | 50 | 182 | Clear Liquid |
| 10/95% Lotion Example #1 + 5% Water | 2 | 50 | 218 | Clear Liquid |
| 11/90% Lotion Example #1 + 10% Water | 2 | 50 | 348 | Clear Liquid |
| 12/85% Lotion Example #1 + 15% Water | 5 | 10 | 4,600 | Viscous gel |
| 13/80% Lotion Example #1 + 20% Water | 5 | 10 | 22,000 (2) | Elastic gel |
| 14/70% Lotion Example #1 + 30% Water | 5 | 10 | 13,000 (2&3) | Crystalline gel |
| 15/50% Lotion Example #1 + 50% Water | 5 | 10 | 3,500 | Viscous turbid gel |
| 16/20% Lotion Example #1 + 80% Water | 2 | 50 | 140 | Turbid emulsion |

It is seen in Table 2 that the water/emulsion mixtures remained a micro-emulsion up to a water concentration of between 10% and 15% by weight of the composition (Examples 9-12). At 15% water, the lotion emulsion turned into a viscous gel, which became even more viscous as additional water was added. At 20% water, the composition was an elastic gel having a viscosity of 22,000 cps, making viscosity measurement difficult. At 30% water (Example 14), the gel exhibited some opacity and appeared to have some crystalline structure appearing almost brittle. Due to the difficulty of viscosity measurement as well as the elastic and adhesive properties of the elastic gel of Example 13, the actual difference in viscosity between Examples 13, 14 may be less than indicated in Table 2.

At 50% by weight water, viscosity fell off dramatically and the composition appeared to be a viscous, turbid gel which was somewhat translucent. While the viscosities of Examples 12 and 15 were similar, the composition of Example 15 exhibited considerably more turbidity. At 80% water, viscosity was low again; however, the composition was no longer clear and appeared to be an emulsion which was somewhat turbid.

Figure 2:
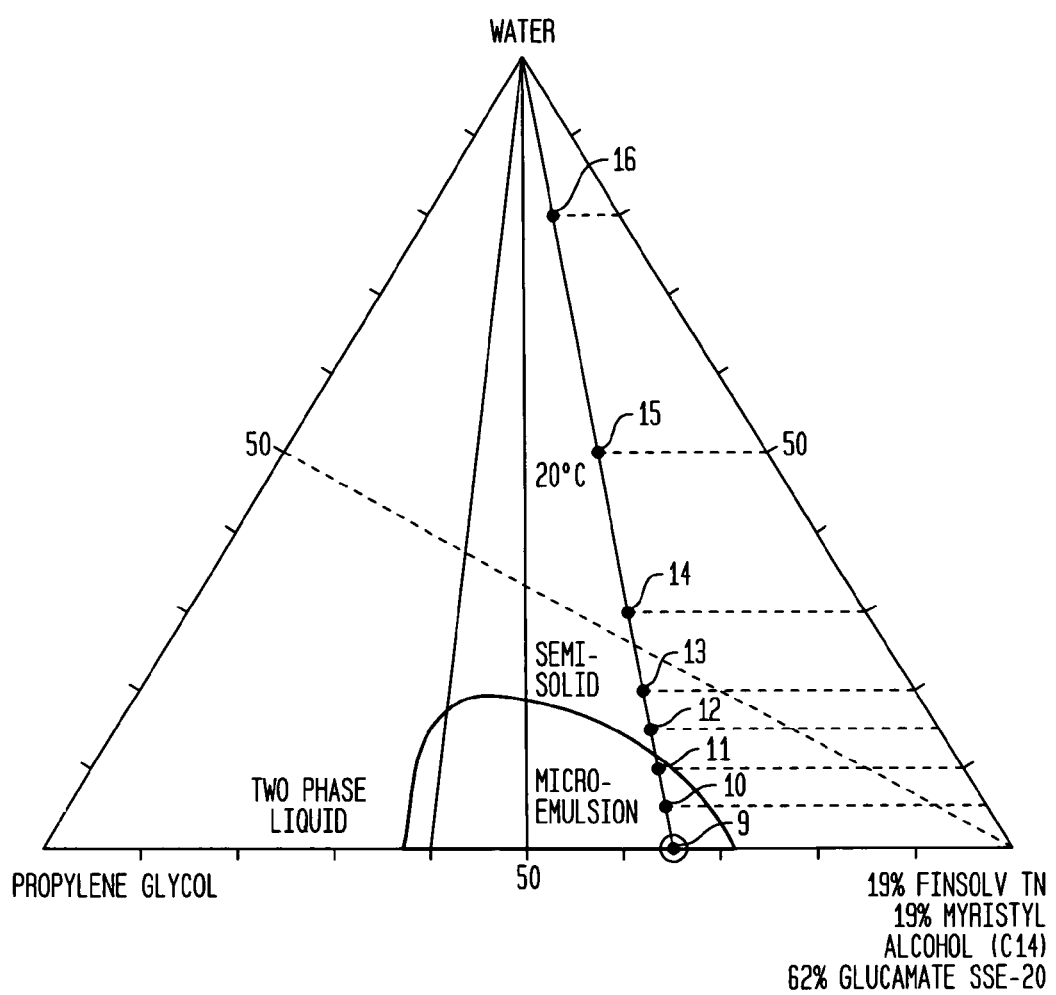
FIG. 2 is a partial phase diagram of the composition of Example I with water showing the phase behavior of a mixture of the composition of Example I with water.

The phase behaviors of the mixtures of Table 2 are illustrated in the partial phase diagram of FIG. 2, where it is seen that Examples 9, 10 and 11 are within the micro-emulsion region of the phase diagram. Examples 12, 13, 14 and 15 are in "semi solid" form, while Example 16 is a two-phase liquid.

Example 17 and Comparative Example A

Still further features of the invention which are highly desirable include WAR delay which promotes lotion transfer to the skin and anti-microbial action of paper towel. These features are appreciated form the discussion which follows.

Towel basesheet was prepared using 100% Douglas Fir Kraft fiber by way of a fabric crepe/Yankee dry process of the class disclosed in co-pending Provisional Application No. 60/693,699, entitled "Fabric-Creped Sheet for Dispensers", filed Jun. 24, 2005, the relevant disclosure of which is incorporated herein by reference in its entirety. To the basesheet, lotion was applied in 1" bands along the machine direction (alternating with 1" bands of unlotioned towel) using a DYNATEC® adhesive applicator of the class seen in U.S. Pat. Nos.: 5,904,298; 5,902,540; and 5,882,573, the disclosures of which are incorporated herein by reference. The lotion formulation of Example 1 was used, containing additionally 2% by weight lotion triclosan anti-microbial compound, 2,4,4'-trichloro-2'- hydroxy diphenyl ether. Further details appear in Table 3 below.

The towel was treated for anti-microbial properties by placing a wetted specimen disk of towel in a Petri dish on inoculated agar. The anti-microbial properties are termed "negative" if microbe contamination is observed on or at the towel after incubation and "positive" if a "ring" around the test specimen is observed, indicating that microbe growth was inhibited by the towel.

Results of anti-microbial testing also appear in Table 3.

TABLE 3

Anti-microbial and Towel Properties

| Properties | Example A No Lotion | Example 17 Lotioned |
|---|---|---|
| Anti-microbial Properties: | | |
| *Staphylococcus aureus* | Negative | Positive |
| *E. coli* | Negative | Positive |
| *Salmonella* sps | Negative | Positive |
| Physical Properties: | | |
| Add on rate (% of product weight) | 0% | 8 to 10% |
| Basis Weight (lbs/rm) | 22.2 | 23.5 |
| Caliper (mils/8 sheets) | 46.0 | 46.1 |
| Dry MD Tensile (g/3") | 6531.2 | 5528.9 |
| Dry CD Tensile (g/3") | 3912.0 | 3435.1 |
| MD Stretch (%) | 7.4 | 7.7 |
| CD Stretch (%) | 3.3 | 3.7 |
| Wet MD Cured Tensile (g/3") (Finch) | 1976.1 | 2040.1 |
| Wet CD Cured Tensile (g/3") (Finch) | 1041.0 | 1122.1 |
| WAR (seconds) (TAPPI) | 34.3 | 67.6 |
| MacBeth 3100 Brightness (%) UV Excluded | 77.5 | 75.5 |
| Opacity (%) | 60.2 | 56.6 |
| SAT Capacity (g/m^2) | 125.1 | 123.0 |
| SAT Time (seconds) | 643.7 | 823.6 |
| GM Break Modulus | 1025.2 | 829.0 |

It is seen in Table 3 that the anti-microbial lotion was effective against *staphylococcus aureous, E.coli* and salmonella sps.

It is also seen that, with the absorbent capacity (SAT) of the control and the lotioned towel remained substantially the same, WAR times, or absorption rates were considerably lengthened, perhaps due to gel blockage; consistent with the data in Table 2 above. Higher WAR values are generally not desired; however, the glutinous gel feel and initial "wetness" experienced by a towel user is a positive consequence, offsetting lower measured absorption rates and encouraging more wiping action so the anti-microbial lotion is more effective in preventing or ameliorating contamination. The apparent gel blockage also appeared to increase CD wet tensile, a common source of towel failure.

While the invention has been described in connection with numerous examples, modifications to those examples within the spirit and scope of the invention will be readily apparent to those of skill in the art. In view of the foregoing discussion, relevant knowledge in the art and references including co-pending applications discussed above, the relevant disclosures of which are all incorporated herein by reference, further description is deemed unnecessary.

What is claimed is:

1. A lotion-treated substrate suitable for tissue or towel comprising:
    (a) a cellulosic web; and
    (b) a lotion emulsion disposed on the web,
the lotion emulsion including a polar emollient and a non-polar emollient as well as a surfactant composition comprising a nonionic surfactant, the polar emollient, nonpolar emollient and surfactant composition being selected so as to be capable of forming a micro-emulsion in the absence of water;
    (c) wherein the lotion emulsion is liquid at room temperature;
    (d) the emollients and surfactant composition are selected such that the lotion emulsion is a stabilized micro-emulsion which undergoes a phase change to a semi-solid or solid upon contact with the fibers of the web and is thus immobilized on the web in a semi-solid or solid state; and
    (e) wherein the lotion emulsion is capable of forming an aqueous gel upon contact with water.

2. The lotion-treated substrate according to claim 1, wherein the polar emollient includes a polar polyhydroxy emollient selected from propylene glycol, glycol, glycerol, sorbitol, diethylene glycol, methylene glycol, polypropylene glycol and polyethylene glycol.

3. The lotion-treated substrate according to claim 1, wherein the non-polar emollient is selected from an aromatic or linear ester, Guerbet ester, mineral oil, squalane, squalene and liquid paraffin.

4. The lotion-treated substrate according to claim 1, wherein the lotion emulsion consists predominantly, 50% by weight or more, of emollient and surfactant.

5. The lotion-treated substrate according to claim 1, wherein the surfactant composition comprises a non-ionic surfactant selected from PEG-20 methyl glucose sesquistearate, PPG-20 methyl glucose ether, PPG-20 methyl glucose ether distearate, PEG-20 methyl glucose distearate, PEG-120 methyl glucose dioleate and ethoxylated methyl glucose having from about 10 to about 20 repeating ethoxy units.

6. The lotion-treated substrate according to claim 1, wherein the surfactant composition comprises a co-surfactant.

7. The lotion-treated substrate according to claim 6, wherein the co-surfactant is a fatty alcohol selected from $C_{12}$-$C_{18}$ fatty alcohols, behenyl alcohol, iso cetyl alcohol and iso stearyl alcohol.

8. The lotion-treated substrate according to claim 1, wherein the lotion emulsion is a waterless micro-emulsion.

9. The lotion-treated substrate according to claim 1, wherein the web is treated with the lotion emulsion in an amount of from about 0.1% to about 25% by weight of the dried fiber.

10. The lotion-treated substrate according to claim 1, wherein the web is treated with the lotion emulsion in an amount of from about 0.5% to about 20% by weight of the dried fiber.

11. The lotion-treated substrate according to claim 1, wherein the lotion emulsion further comprises an anti-microbial agent.

12. The lotion-treated substrate according to claim 11, comprising an anti-microbial agent selected from: 2,4,4'-trichloro-2'-hydroxydiphenyl ether; 3,4,4'-trichlorocarbanilide; 3,4,4'-trifluoromethyl-4,4'-d-ichlorocarbanilide; 5-chloro-2-methyl-4-isothiazolin-3-one; iodopropynlbutylcarbamate; 8-hydroxyquinoline; 8-hydroxyquinoline citrate; 8-hydroxyquinoline sulfate; 4-chloro-3,5-xylenol; 2-bromo-2-nitropropane-1,3-diol; butoconazole; nystatin; terconazole; nitrofurantoin; phenazopyridine; acyclovir; clortrimazole; chloroxylenol; chlorhexidine; chlorhexidine gluconate; miconazole; terconazole; butylparaben; ethylparaben; methylparaben; methylchloroisothiazoline; methylisothiazoline and mixtures thereof.

13. The lotion-treated substrate according to claim 1, wherein the lotion emulsion further comprises an additive selected from the group of fragrances, preservatives, medicinal agents, humectants, natural therapeutic oils, botanical extracts, natural or synthetic powders, and soothing agents.

14. The lotion-treated substrate according to claim 13, wherein the additive comprises a fragrance.

15. The lotion-treated substrate according to claim 1, wherein the web comprises a wet strength agent.

16. A lotion-treated substrate suitable for tissue or towel comprising:
(a) a cellulosic web;
(b) a waterless micro-emulsion which is liquid at room temperature and undergoes a phase change to a semi-solid or solid upon contact with the fibers of the web and is thus immobilized on the web in a semi-solid or solid state;
(c) wherein the waterless micro-emulsion is a stabilized micro-emulsion which consists essentially of a polar emollient, a non-polar emollient and a surfactant composition comprising a nonionic surfactant; and
(d) wherein further the waterless micro-emulsion is capable of forming an aqueous gel upon contact with water.

17. The lotion-treated substrate according to claim 16, wherein the waterless micro-emulsion comprises a polar polyhydroxy emollient selected from propylene glycol, glycol, glycerol, sorbitol, diethylene glycol, methylene glycol, polypropylene glycol and polyethylene glycol.

18. The lotion-treated substrate according to claim 16, wherein the waterless micro-emulsion comprises a non-polar emollient selected from an aromatic or linear ester, Guerbet ester, mineral oil, squalane, squalene and liquid paraffin.

19. The lotion-treated substrate according to claim 16, wherein the waterless micro-emulsion comprises a non-ionic surfactant selected from PEG-20 methyl glucose sesquistearate, PPG-20 methyl glucose ether, PPG-20 methyl glucose ether distearate, PEG-20 methyl glucose distearate, PEG-120 methyl glucose dioleate and ethoxylated methyl glucose having from about 10 to about 20 repeating ethoxy units.

20. A lotion-treated substrate suitable for tissue or towel comprising:
(a) a cellulosic web; and
(b) a waterless micro-emulsion which is liquid at room temperature and undergoes a phase change to a semi-solid or solid upon contact with the fibers of the web and is thus immobilized on the web in a semi-solid or a solid state;
wherein the micro-emulsion is a stabilized micro-emulsion which comprises a polar emollient, a non-polar emollient, a co-surfactant and a non-ionic surfactant.

21. The lotion-treated substrate according to claim 20, wherein the co-surfactant is a fatty alcohol.

22. The lotion-treated substrate according to claim 21, wherein the fatty alcohol is selected from $C_{12}$-$C_{18}$ fatty alcohols, behenyl alcohol, iso cetyl alcohol and iso stearyl alcohol.

23. A method of making a lotion-treated substrate suitable for tissue or towel comprising:
(a) preparing a lotion emulsion including a polar emollient and a non-polar emollient as well as a surfactant composition comprising a nonionic surfactant, the polar emollient, nonpolar emollient and surfactant composition being selected so as to be capable of forming a micro-emulsion in the absence of water;
(b) treating a cellulosic web with the lotion emulsion;
wherein the emollient composition and surfactant composition are further characterized such that the lotion emulsion is a stabilized micro-emulsion which undergoes a phase change to a semi-solid or solid upon contact with the fibers of the web and is thus immobilized on the towel web in a semi-solid or solid state and wherein the lotion emulsion is capable of forming an aqueous gel upon contact with water.

24. The method of making a lotion-treated substrate according to claim 23, wherein the lotion emulsion is applied to the web by way of spraying or printing.

25. The method of making a lotion-treated substrate according to claim 23, wherein the emollient composition comprises a polar polyhydroxy emollient selected from propylene glycol, glycol, glycerol, sorbitol, diethylene glycol, methylene glycol, polypropylene glycol and polyethylene glycol.

26. The method of making a lotion-treated substrate according to claim 23, wherein the emollient composition comprises a non-polar emollient selected from an aromatic or linear ester, Guerbet ester, mineral oil, squalane, squalene and liquid paraffin.

27. The method of making a lotion-treated substrate according to claim 23, wherein the surfactant composition comprises a non-ionic surfactant selected from PEG-20 methyl glucose sesquistearate, PPG-20 methyl glucose ether, PPG-20 methyl glucose ether distearate, PEG-20 methyl glucose distearate, PEG-120 methyl glucose dioleate and ethoxylated methyl glucose having from about 10 to about 20 repeating ethoxy units.

28. The method of making a lotion-treated substrate according to claim 23, wherein the surfactant composition comprises a co-surfactant selected from $C_{12}$-$C_{18}$ fatty alcohols, behenyl alcohol, iso cetyl alcohol and iso stearyl alcohol.

29. The method of making a lotion-treated substrate according to claim 23, wherein the lotion emulsion further comprises an additive selected from the group of preservatives, medicinal agents, humectants, fragrances, natural therapeutic oils, botanical extracts, natural or synthetic powders, and soothing agents.

30. The method of making a lotion-treated substrate according to claim 23, comprising treating the cellulosic web with lotion emulsion in an amount of from about 0.1% to about 25% by weight of the dried fiber.

31. The method of making a lotion-treated substrate according to claim 23, comprising treating the cellulosic web with lotion emulsion in an amount of from about 0.5% to about 20% by weight of the dried fiber.

32. A lotion-treated substrate suitable for tissue or towel comprising:
(a) a cellulosic web; and
(b) a lotion emulsion disposed on the web,
the lotion emulsion including a polar emollient and a non-polar emollient as well as a surfactant composition comprising a nonionic surfactant, the polar emollient, nonpolar emollient and surfactant composition being selected so as to be capable of forming a micro-emulsion in the absence of water;
(c) wherein the lotion emulsion is liquid at room temperature;
(d) the emollients and surfactant composition are selected such that the lotion emulsion is a stabilized micro-emulsion which undergoes a phase change to a semi-solid or solid upon contact with the fibers of the web and is thus immobilized on the web in a semi-solid or solid state; and
(e) wherein the lotion emulsion is capable of forming an aqueous gel upon contact with a sufficient amount of water; and
(f) wherein further the lotion emulsion is also capable of forming a micro-emulsion in the presence of water in an amount less than required for gellation.

* * * * *